US010436679B2

(12) United States Patent
Brooks et al.

(10) Patent No.: US 10,436,679 B2
(45) Date of Patent: Oct. 8, 2019

(54) AIR MANAGEMENT SYSTEM FOR SMOKING MACHINES

(71) Applicant: Molins PLC, Milton Keynes (GB)

(72) Inventors: Nigel Paul Brooks, Bedford (GB); Peter Francis Jordan, Northampton (GB)

(73) Assignee: MPRD LIMITED, Milton Keynes (GB)

( * ) Notice: Subject to any disclaimer, the term of this patent is extended or adjusted under 35 U.S.C. 154(b) by 147 days.

(21) Appl. No.: 15/059,908

(22) Filed: Mar. 3, 2016

(65) Prior Publication Data
US 2016/0187233 A1    Jun. 30, 2016

Related U.S. Application Data

(63) Continuation of application No. PCT/GB2014/052649, filed on Sep. 2, 2014.

(30) Foreign Application Priority Data

Sep. 5, 2013    (GB) .................................. 1315820.9

(51) Int. Cl.
| | |
|---|---|
| *G01N 1/22* | (2006.01) |
| *G01N 1/24* | (2006.01) |
| *G01N 33/00* | (2006.01) |
| *A24C 5/34* | (2006.01) |

(52) U.S. Cl.
CPC ............. *G01N 1/2247* (2013.01); *A24C 5/34* (2013.01); *A24C 5/3406* (2013.01); *G01N 1/24* (2013.01); *G01N 33/0098* (2013.01)

(58) Field of Classification Search
CPC ................................ G01N 1/24; G01N 1/2247

USPC ...................................................... 73/863.21
See application file for complete search history.

(56) References Cited

U.S. PATENT DOCUMENTS

| | | | |
|---|---|---|---|
| 3,548,840 A | 12/1970 | Baumgartner | |
| 3,548,841 A * | 12/1970 | Caughey | A24C 5/3406 131/175 |
| 4,090,320 A | 5/1978 | Grant | |
| 4,119,419 A * | 10/1978 | Passaro | A24F 19/0042 131/238 |
| 4,400,972 A | 8/1983 | Grant | |
| 5,113,689 A | 5/1992 | Grant | |

(Continued)

FOREIGN PATENT DOCUMENTS

| | | |
|---|---|---|
| CN | 201967629 U | 9/2011 |
| EP | 0417974 A1 | 3/1991 |

(Continued)

OTHER PUBLICATIONS

ISO 3308; International Standard; Fith Edition; Oct. 15, 2012.*
(Continued)

*Primary Examiner* — John Fitzgerald
*Assistant Examiner* — Rodney T Frank
(74) *Attorney, Agent, or Firm* — Woodard Emhardt Henry Reeves & Wagner LLP

(57) ABSTRACT

An ashtray is disclosed for use with a smoking machine for smoking a smoking article. The ashtray comprises directional fins underneath the ashtray for directing airflow over the smoking article. This can allow the direction of airflow to be confined to a well-defined path, and turbulence in the airflow to be reduced.

29 Claims, 6 Drawing Sheets

(56) References Cited

U.S. PATENT DOCUMENTS 6,116,246 A * 9/2000 Glenn ................. A24F 19/0042
                                                        131/231
6,227,400 B1   5/2001 Paladino

FOREIGN PATENT DOCUMENTS

JP          10174622 A    6/1998
NL          1018585 C2    1/2003

OTHER PUBLICATIONS

International Search Report from PCT/GB2014/052649 dated Jul. 1, 2015.
UK Search Report from GB1315820.9 dated Feb. 20, 2014.

* cited by examiner

AIR MANAGEMENT SYSTEM FOR SMOKING MACHINES

CROSS REFERENCE TO RELATED APPLICATIONS

This application is a continuation of International Application No. PCT/GB2014/052649 filed Sep. 2, 2014 which claims priority to GB1315820.9 filed Sep. 5, 2013, both of which are hereby incorporated by reference.

FIELD OF THE INVENTION

The present invention relates to techniques for managing the flow of air within a smoking machine.

BACKGROUND

Cigars, cigarettes, and cigarillos (generally known as smoking articles) may be analysed for the composition of the smoke that they produce using a device known as a smoking machine. A smoking machine typically comprises at least one holder for holding a smoking article, and a puffing means for drawing air in a controlled fashion through the smoking article as it burns. The smoke drawn from the smoking article is referred to as mainstream smoke and is collected for further analysis. The smoke generated between puffs is referred to as sidestream smoke, and is usually conveyed away from the cigarette using an air extraction system. An ash tray may be provided to collect the ash produced by the smoking article as it burns.

The results obtained by analysing the composition of the mainstream smoke may be used in characterising the smoking article, or by regulators to determine the yield of smoke components and whether the smoking article is below a predefined ceiling for each component. Since the smoking article is destroyed during the process of smoking it is imperative that the process of smoking is controlled adequately and repeatably to ensure meaningful comparisons can be made between brands and against standards. Consequently the machines used are defined in part by international standards of design and construction such as ISO3308:2012 (International Standards Organisation standard "routine analytical smoking machine—definitions and standard conditions). One of the features of the smoking machine design is the control of air flow over the smoking article during smoking, and this is typically required to be of a particular magnitude.

In a common type of smoking machine where the articles to be smoked are placed side by side in a straight line (a linear smoking machine) the direction of airflow is intended to be along the smoking portion of the smoking article. However in practice the airflow may be at an angle to the axis of the smoking article. This angle may vary from article to article depending on the position within the line of smoked articles and the extraction system employed to remove the smoke. Moreover, known smoking machines may introduce some turbulence in the airflow. These effects may have an impact on the uniformity of the smoking process and on the absolute magnitude of the yield from the smoking article.

Previous attempts at controlling the flow of air over the smoking article have included providing a diffusing plate above the smoking article (commonly known as a Burgess plate), and using variable controlled air extraction. However there remain some inconsistencies in air flow between machines and also within individual machines.

SUMMARY

According to a first aspect of the present invention there is provided an ashtray for a smoking machine for smoking a smoking article, the ashtray comprising a directional fin for directing airflow over the smoking article.

By providing an ash tray with a directional fin for directing airflow, the present invention may provide the advantage that the direction of airflow in the smoking machine may be confined to a well-defined path and/or turbulence in the airflow may be reduced. This may improve the uniformity of the smoking process and help to confine differences in measurement to those in construction of the smoking article.

Preferably the directional fin (in conjunction with the ashtray) is arranged to guide the flow of air along the axis of the smoking article. This can help to ensure consistency in the smoking process, by reducing angular components of the airflow (i.e. components which are at an angle to the axis of the smoking article) and/or turbulence. In order to help achieve this, the directional fin may run substantially parallel to the axis of the smoking article.

Typically air is drawn into a smoking machine through a void under the ashtray and from the space in front of the smoking article. Thus the directional fin may be at least partially located beneath the ashtray and/or at least partially on the leading edge of the ashtray. This can assist in directing the flow of air around the ashtray. For example, the directional fin may be a projection from or appendage to the bottom of the ashtray. Preferably the directional fin is in the form of a lobe which extends beneath the ashtray.

Preferably the ashtray has a main body which defines a container, such as a channel or a bowl, for collecting ash. It will be appreciated that the bottom surface of the container should be continuous, in order to prevent ash from falling through.

Preferably the ashtray is located beneath a smoking position, in order to collect ash falling from a smoking article. The ashtray may be removable in order to allow the collected ash to be discarded.

In order to support the directional fin and/or to assist with directing airflow, the ashtray may comprise a lower member which extends beneath and rearwards of the ashtray main body. In this case the directional fin may be at least partially located on the lower member.

The directional fin may have a width which decreases with distance away from the ashtray. For example, the directional fin may be wedge-shaped. This may help to ensure that the fin is stable and effective in directing airflow.

Preferably the directional fin forms a smooth surface with the ashtray. This, together with the directional nature of the fin, can help to minimise turbulence in the airflow.

The directional fin may comprise a fin body, a tapered guide into the fin, and/or a tapered guide out of the fin. The tapered guides may help to ensure the smooth flow of air past the fin, and thus help to reduce turbulence.

Preferably a directional fin is located either side of a smoking position. Thus, in use, there may be a directional fin below and either side of a smoking article which is being smoked in the smoking machine. This may help to reduce angular components of the airflow and/or turbulence.

Preferably the ashtray is arranged to direct airflow from under the ashtray, around a lip of the ashtray, and to the smoking article. Preferably the lip of the ashtray is curved. This may assist with the smooth transit of air around the ashtray.

It has been found that, in a conventional smoking machine, turbulence may be introduced into the airflow by, amongst other things, a void under the ashtray. In a preferred embodiment of the invention, an air scoop is provided for deflecting airflow around the bottom of the ashtray. This can allow air to flow smoothly around the bottom of the ashtray, thereby minimising turbulence and improving the uniformity of the smoking process.

Where the ashtray comprises a lower member, the lower member may have a surface which is a continuation of the surface of the air scoop.

The smoking machine may be arranged to smoke a plurality of smoking articles, and thus the ashtray may be arranged to collect the ash from a plurality of smoking articles. For example, the ashtray may have an elongated form which allows it to collect the ash from a plurality of smoking articles which are placed side by side in a linear smoking machine. The ashtray may comprise a plurality of directional fins for directing airflow over the smoking articles. The directional fins are preferably regularly spaced along the leading edge of the ashtray. For example, a directional fin may be located between each smoking position, and at each end.

According to another aspect of the present invention there is provided a smoking machine comprising an ashtray in any of the forms described above. The smoking machine is preferably arranged to collect mainstream smoke. Preferably the machine further comprises an air extraction system, and a holder for holding each smoking article.

As discussed above, the directional fins may conveniently be a projection from or appendage to the bottom of the ashtray. However, it would also be possible for the fins to be separate from the ashtray. Thus, according to another aspect of the invention, there is provided a smoking machine for smoking a plurality of smoking articles, the machine comprising a plurality of holders for holding the smoking articles, an air extraction system, and a plurality of directional fins for directing airflow over the smoking articles.

Preferably a directional fin is located between each smoking position. A directional fin may also be located between a final smoking position and an outer wall of the smoking machine.

The smoking machine may further comprise an ashtray for catching ash from the smoking articles. The directional fins may form part of the ashtray, or they may be provided separately, or a combination of the two. For example, the directional fins may be part of a separate member, or they may be attached to a wall of the smoking machine, or to an air scoop.

A conventional smoking machine has a number of ducts for extracting air from the smoking area. It has been found that, by providing the directional fins of the present invention, it may be possible to eliminate the ducts, and provide an open ducting arrangement with a single extraction source. This can allow the air extraction system to be simplified, thereby reducing the cost. Thus the air extraction system may comprise an open ducting arrangement with a single extraction source. In this case balancing baffles may be provided to balance the flow of air over the smoking articles.

The smoking machine may comprise an ashtray and an air scoop for deflecting airflow around the bottom of the ashtray. The air scoop may reduce the amount of turbulence in the airflow.

The air scoop may be provided independently of the directional fins. Thus, according to another aspect of the invention, there is provided a smoking machine for smoking a plurality of smoking articles, the machine comprising a plurality of holders for holding the smoking articles, an air extraction system, an ashtray for catching ash from the smoking articles, and an air scoop for deflecting airflow around the bottom of the ashtray.

In any of the above arrangements the smoking machine may further comprise puffing means for drawing air through the smoking articles as they burn, in order to smoke the smoking articles.

Corresponding methods may also be provided and thus, according to another aspect of the present invention there is provided a method of managing air flow in a smoking machine while smoking a smoking article, the method comprising directing air flow along the axis of the smoking article using a directional fin.

Preferably airflow is directed from under an ashtray, around a lip of the ashtray and to the smoking article.

The directional fin may form part of an ashtray. The method may further comprise directing air flow under the ashtray using an air scoop.

Features of one aspect of the invention may be provided with any of the other aspects. Any of the apparatus features may be provided as method features and vice versa.

BRIEF DESCRIPTION OF THE DRAWINGS

Preferred features of the present invention will now be described, purely by way of example, with reference to the accompanying drawings, in which.

DESCRIPTION OF THE SELECTED EMBODIMENTS

Figure 1:
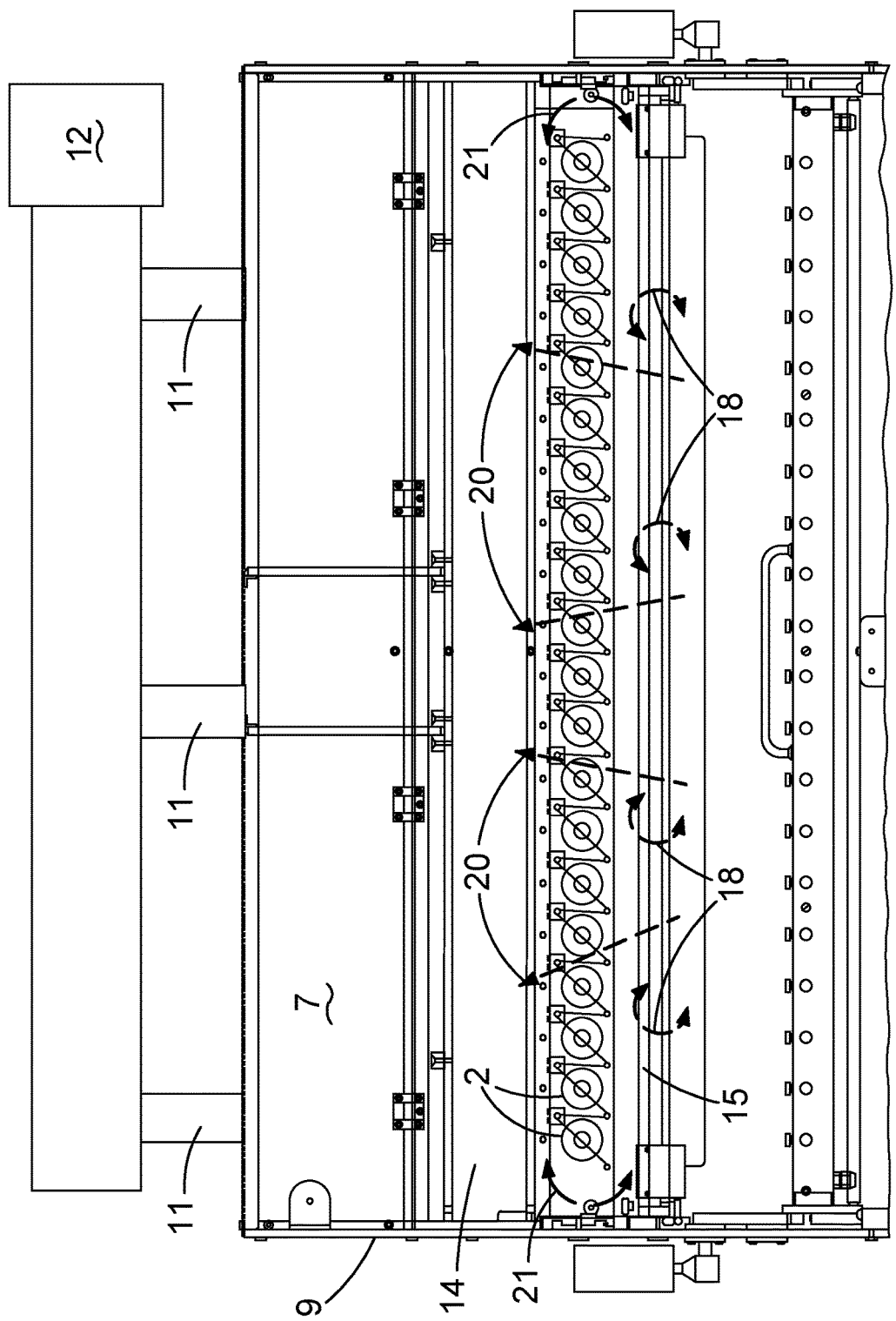
FIG. 1 is a perspective view of a typical smoking machine.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

FIG. 1 shows a perspective view of a typical linear smoking machine. The machine comprises a plurality of holders 2 each of which holds a cigarette or other smoking article (sometimes referred to as the "rod"). A puffing mechanism draws air in a controlled fashion through the smoking articles as they burn. A perforated sheet known as the Burgess plate or straw plate is provided above the smoking articles. The perforated sheet communicates with a duct 7, which in turn is connected to extraction ducts 11 and extraction fan 12. In operation, the fan 12 draws air through the ducts 7, 11 and away from the smoking article, together with any noxious gases or products of combustion known as sidestream smoke. A flap 14 is provided that restricts air flow and reduces the requirements for extraction. This flap is normally removed when access to the smoking articles is needed. The smoking area is enclosed by a hood 9 or other enclosure, to ensure that the air is extracted through the ducts 7, and that there are no cross currents of air. An ashtray 15 is situated beneath the smoking articles. The ashtray has an elongated form with a trough or series of bowls under the smoking positions for collecting ash from the smoking articles.

When a smoking article is smoked, the magnitude of airflow impacts on the burning process, and the direction of airflow also can affect the yields of smoke constituents such as carbon monoxide (CO) and nicotine free dry particulate matter (NFDPM) often referred to as "tar". Furthermore, turbulent flow within the area where the smoking article undergoes combustion can change the measured yields of the smoking article and is therefore undesirable.

In a linear smoking machine such as that shown in FIG. 1 the direction of air flow is intended to be along the smoking portion of the smoking article, and upwards at the rear over the un-smoked portion of the rod. However in practice the air flow may be at an angle to the axis of the smoking article. This angle is not consistent from rod to rod depending on the position within the line of smoked rods and the exact extraction system employed to remove the smoke. There is a tendency for smoke to be drawn obliquely towards the smoke extraction ducts. Moreover, at the edges of the enclosure of the smoking articles there are edge effects where air changes speed near the surfaces and causes turbulent flow for those rods smoked at the edges of the machine.

In FIG. 1, angular components of the air flow toward the extraction vents 7 are shown by arrows 20. There is some turbulent flow at the point of restriction of the air flow between the flap 14 and ashtray 15, as shown by the arrows 18. The smoking articles close to the edge of the smoking hood 9 are subjected to additional turbulence, as indicated by arrows 21.

Turbulence is not confined to the machine edges and turbulent flow can occur along the row of smoked samples. This is exacerbated by the open nature of the air intake area which is commonly crossed by operators and others during use which causes eddies in the air flow and so introduces a degree of non-uniformity of combustion, smoldering and pyrolysis during both puffing and the between puffing portions of mechanical smoking known as the free-burn state.

The air consumed for smoking is drawn in part from the dead space under the ashtray (a device defined by standards) and some additional turbulence is introduced as the air accelerates when moving around the lip of the ashtray.

The direction of air flow and uniformity of the flow can be visualised by the release of smoke into the air flow in a controlled and gentle stream using a smoke generator such as a Drager tube or vaporising propylene glycol through a fine nozzle. A record of flow direction and stability can be made using a commercially available video recording device.

Figure 2:
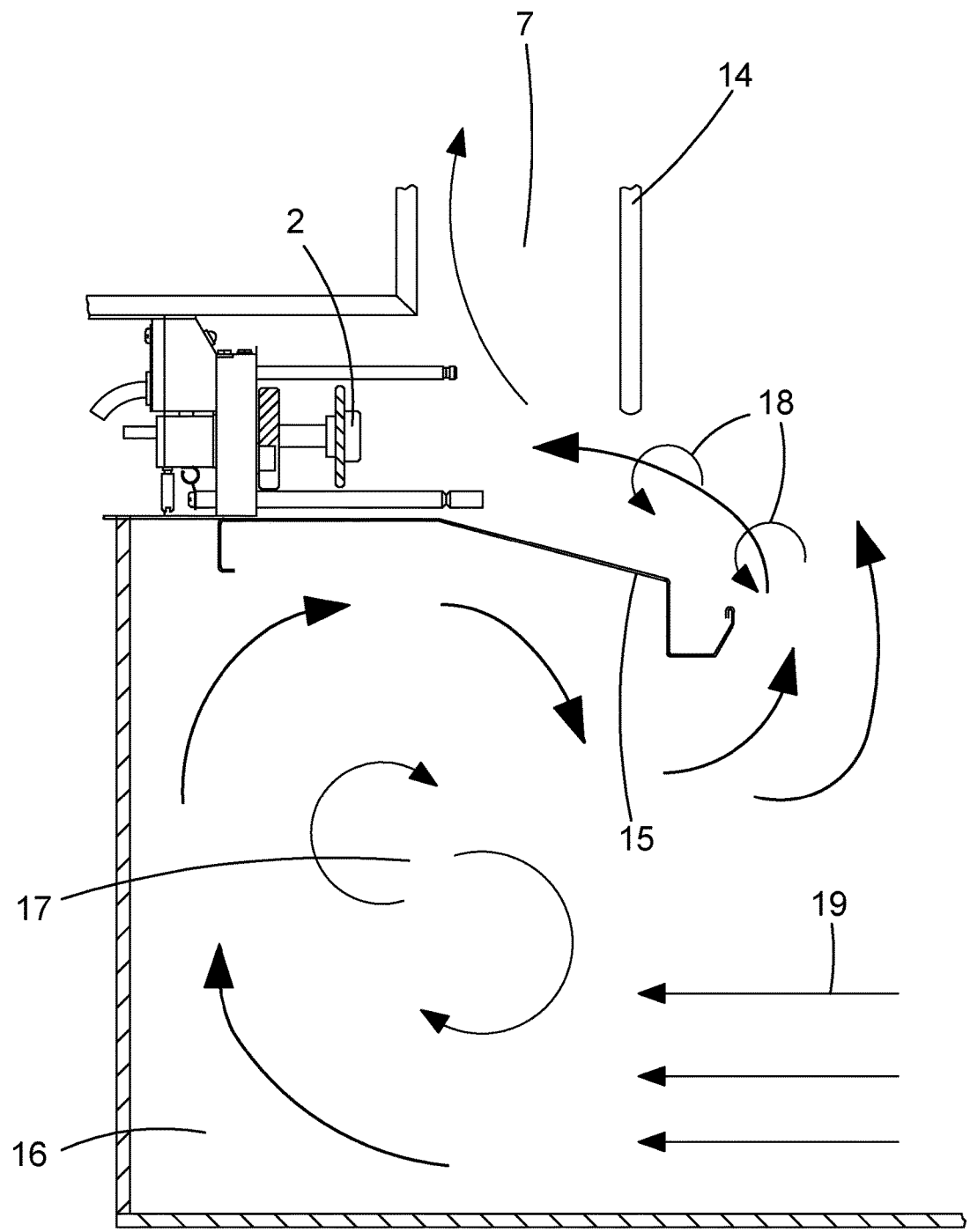
FIG. 2 is a cross-sectional view through part of the smoking machine of FIG. 1.

FIG. 2 is a cross-sectional view through part of the smoking machine of FIG. 1, showing typical air flows through the machine. Referring to FIG. 2, air is drawn in to the region under the ashtray 15 as shown by arrows 19. Due to the nature of the void under the formed space 16, the air is subject to churning 17 and so is predisposed to be turbulent before exiting the void. The air then moves across the lip of the ashtray 15 and across the smoking article through to the extraction system 7. There is some turbulent flow 18 at the point of restriction of flow between the flap 14 and ashtray 15. This is exacerbated by an angular flow component 20 toward the extraction vents (see FIG. 1).

Figure 3:
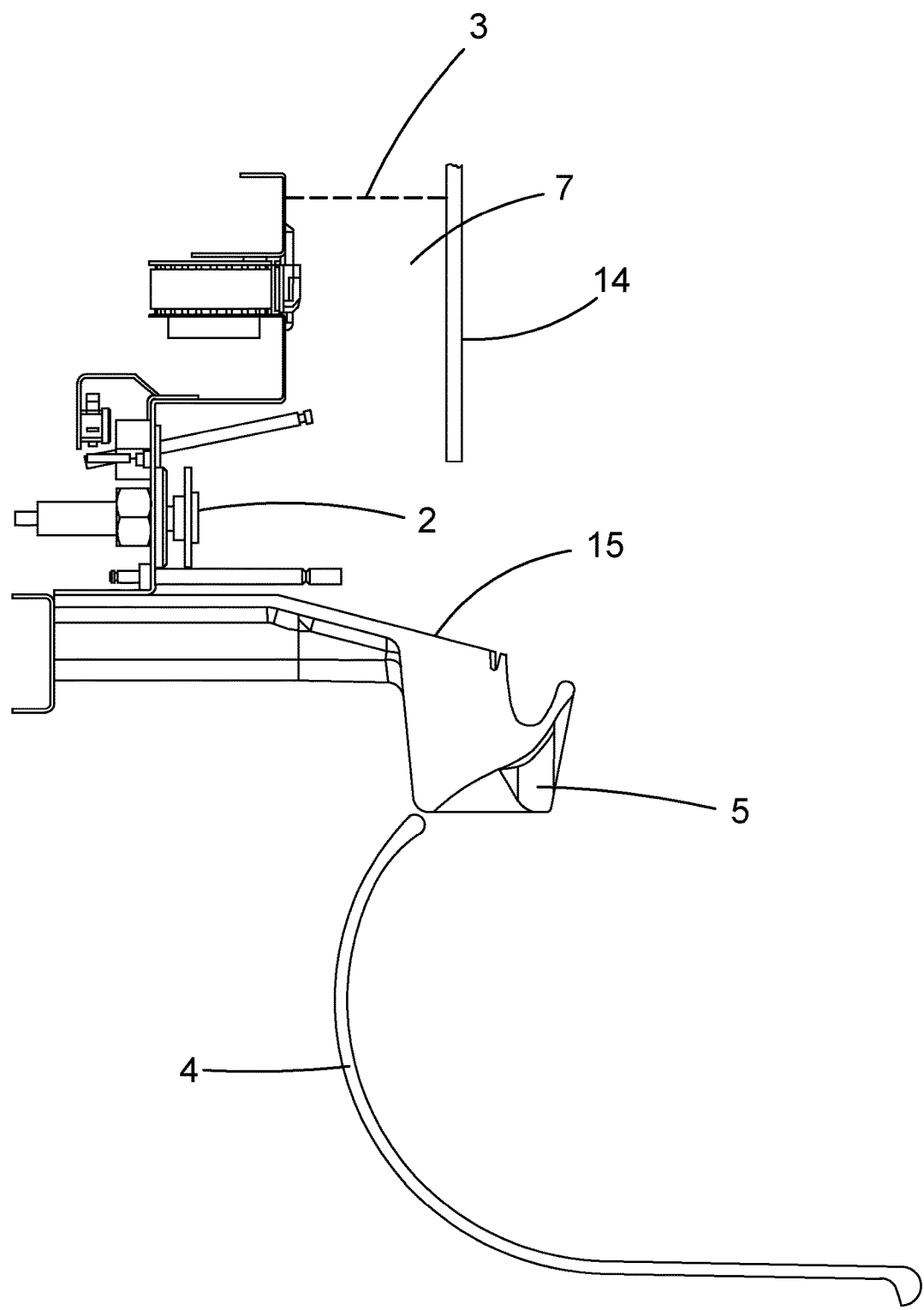
FIG. 3 is a cross-sectional view through part of a smoking machine in accordance with an embodiment of the invention.

FIG. 3 is a cross-sectional view through part of a smoking machine in accordance with an embodiment of the invention. Referring to FIG. 3, the cigarette or other smoking article is held in a holder 2, which may be the same as in a conventional smoking machine. Above the cigarette is a Burgess plate 3 located in a duct 7 which in turn is connected to extraction ducts 11 and extraction fan 12. The Burgess plate is a horizontal perforated sheet held between two vertical surfaces and designed to straighten airflow. Situated beneath the smoking article 10 is an ashtray 15 with an angular form.

The ashtray 15 of FIG. 3 comprises a number of directional fins 5 that form the basis of an air controlling mechanism. The fins 5 are thin projections or appendages on the bottom of the ashtray 15. The fins form a smoothed surface with the edge of the ashtray return, the profile assisting the smooth transit of air from beneath the ashtray over the smoking article. The size and shape of the fins can be optimised for different rod spacings, air flow magnitudes and different geometries of the smoking machine.

In the arrangement of FIG. 3 a curved air scoop 4 is provided under the ashtray. The air scoop 4 is designed to control the flow of air over the directional fins 5. The air scoop 4 directs air entering the lower part of the smoking machine around the ashtray and between the fins 5. The air scoop 4 thus reduces the turbulence in the airflow in comparison to the conventional arrangement shown in FIG. 2.

Figure 4:
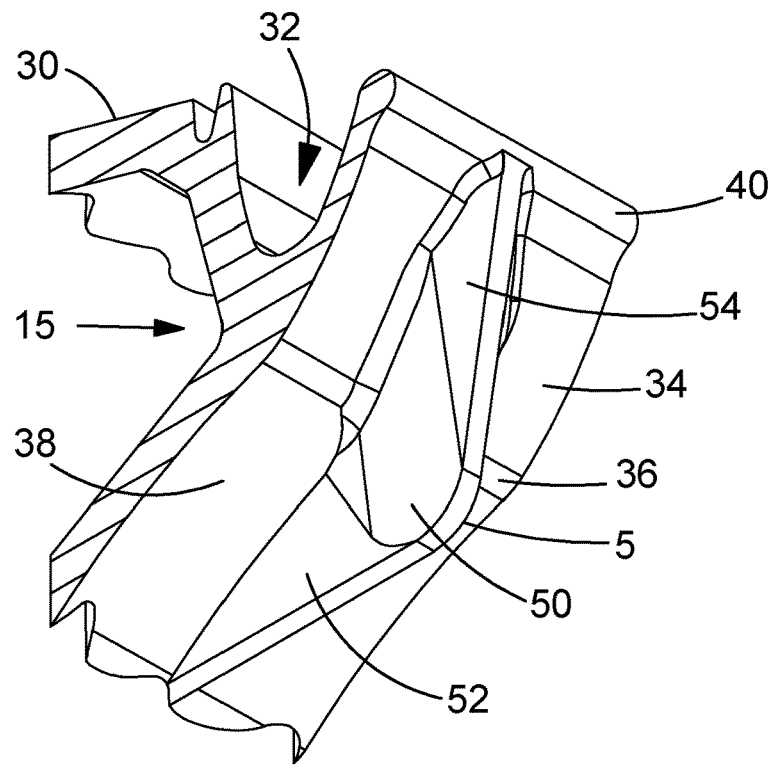
FIG. 4 is a perspective view of part of an ashtray with a directional fin in accordance with an embodiment of the invention.

FIG. 4 shows a perspective view of part of the ashtray 15 with a directional fin 5 in accordance with an embodiment of the invention. Referring to FIG. 4, the ashtray comprises an ashtray surface 30, an ash collection channel 32, a leading edge 34 with a curved lip 40, and a bottom edge 36. In this embodiment the ashtray also includes a lower member 38 which extends beneath and rearwards of the main body of the ashtray, forming a profile which is a continuation of the profile of the air scoop 4. The lower member 38 provides support for the fin 5 and helps to direct airflow from beneath the ashtray. A cross-sectional view through the ashtray of FIG. 4 is shown in FIG. 5.

Figure 5:
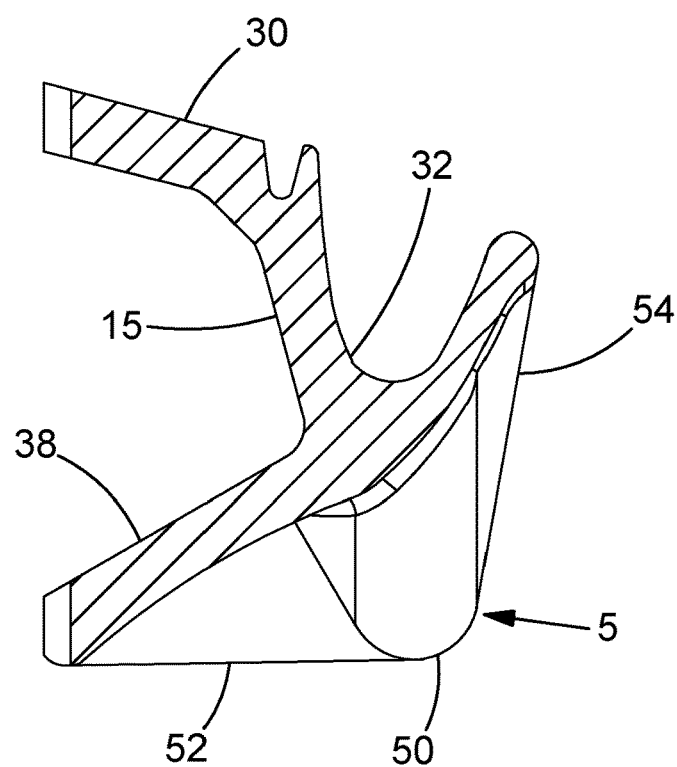
FIG. 5 is a cross-sectional view through the ashtray of FIG. 4.

Referring to FIGS. 4 and 5, the directional fin 5 protrudes from beneath the ashtray, extending from the leading edge 34, across the bottom of the ashtray 36 and the lower member 38. In this example, the fin 5 occupies a sector of space of approximately 90°. The fin is wedge-shaped in form, with a width that decreases with distance away from the ashtray.

In the arrangement of FIGS. 4 and 5, the fin 5 comprises a fin body 50 with a tapered guide 52 into the fin and a tapered guide 54 out of the fin. The tapered guides 52, 54 help to ensure the smooth flow of air past the fin, and thus help to reduce turbulence. In practice any burrs or sharp edges may be removed, so that surfaces of the fin and the underside of the ashtray are smooth.

Figure 6:
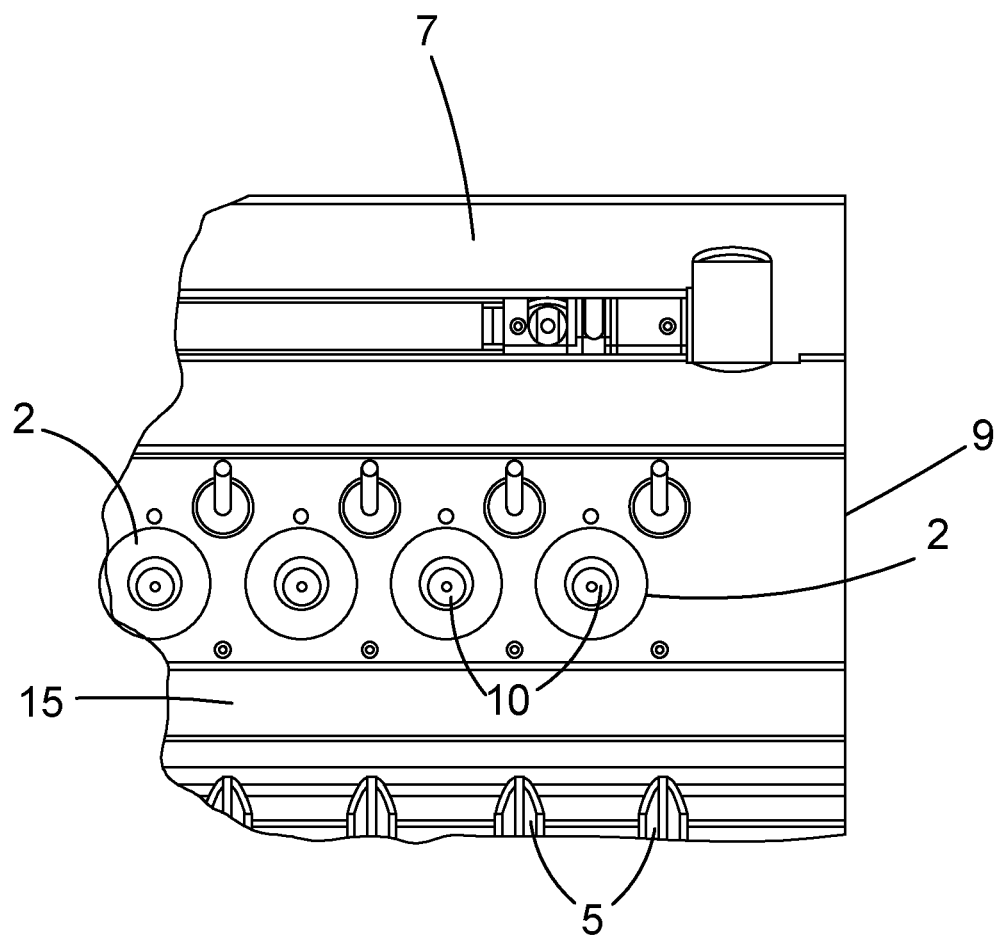
FIG. 6 is a front elevation view of part of the smoking machine of FIG. 3.

FIG. 6 is a front elevation view of part of the smoking machine, showing the location of the fins. Referring to FIG. 6, a plurality of holders 2 is provided for holding smoking articles 10. The fins 5 are regularly spaced along the leading edge of the ashtray 15. A directional fin 5 is located between each smoking port position, with a final fin being located between the final smoking article and the outer wall of the smoking machine enclosure 9.

In the arrangement of FIGS. 3 to 6, the air scoop 4 and directional fins 5 guide the air flow from the front of the smoking area and direct the air without excessive turbulence over the smoking article and into the smoke extraction duct 7. The fins 5 direct the air flow along the axis of the smoking article, thus reducing or eliminating any angular component of the air flow. As a consequence, the direction and strength of the airflow is less sensitive to the relative location and strength of the extraction ducts 11. The directional fins 5 also help to eliminate the edge effects of the smoking machine enclosure.

It has been found that that the fins 5 make the direction of airflow less sensitive to the positioning and relative strength of air extraction for multiple ducted systems of extraction. This can allow a multiple extraction system to be replaced by a single open ducting arrangement with a single extraction source and balancing baffles.

The directional fins 5 and air scoop 4 can be made of any suitable rigid or semi rigid material, such as a moulded heat resistant plastic.

Figure 7:
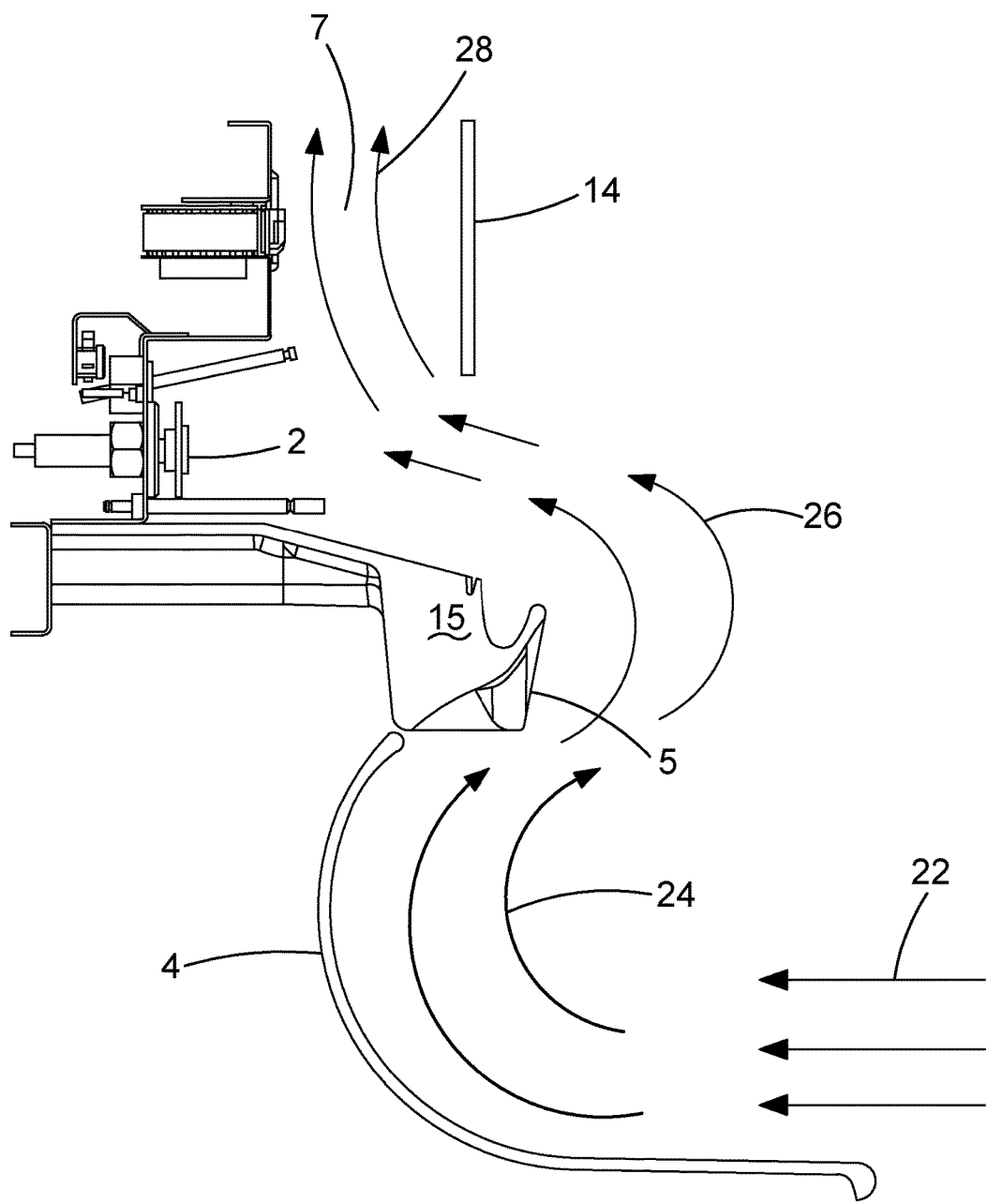
FIG. 7 is typical air flows through the smoking machine.

FIG. 7 is a cross-sectional view through part of the smoking machine of FIGS. 3 to 6, showing typical air flows through the machine. Referring to FIG. 7, air is drawn in to the region under the ashtray 15, as indicated by arrows 22. The air is then deflected around the bottom of the ashtray by the air scoop 4, as indicated by arrows 24. The air scoop 4 provides a smooth path for the air flow, and minimises any turbulence. The air then moves across the lip of the ashtray 5 and across the smoking article as indicated by arrows 26. The directional fins 5 on the underside of the ashtray 15 assist the smooth transit of air from beneath the ashtray over the smoking article, thus minimising turbulence. Furthermore, the directional fins 5 minimise any angular component of the air flow towards the extraction vents. Thus a controlled, directed and un-agitated airflow is provided across the smoking article. The air is then extracted through the vent 7, as indicated by arrows 28, and is safely expelled to the atmosphere or collected for analysis.

For ease of access and for the purposes of service and cleaning the whole ashtray and air direction mechanism may be lowered and removed.

To further restrict and control air flow a flap 14 is present in the design that restricts flow and reduces the requirements for extraction. This flap is normally removed when access is needed for the smoking articles.

In the described system, access is retained to the smoking articles, a feature desirable for any practical implementation of a smoking machine as the loading, unloading, lighting, termination and butt removal operations may all need to be conducted whilst other smoking articles are alight and being puffed.

The embodiments described above provide air flow management within a smoking machine with the intent of producing a controlled, directed and un-agitated air flow across a smoking article.

In the examples shown the directional fins are used in conjunction with an air scoop which presents air with reduced turbulence to the fins. However use can be made of the directional fins without the addition of an air scoop with consequent improvements in turbulence and flow, albeit of a lesser degree. Likewise, the air scoop could be used without the directional fins, to reduce turbulence in the smoking machine.

Although described for a linear smoking machine where the smoking articles are placed in a line and side by side, the directional fins and/or air scoop can be applied to other smoking machine geometries such as, but not limited to, a system where the smoking articles are deployed in a ring or circle and moved to a puffing device with the smoking articles either facing outwards or inwards from or to the centre of the ring.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. An ashtray constructed and arranged for use with a smoking machine which is constructed and arranged for holding a smoking article, said ashtray comprising:
a directional fin which is attached to and/or integral with said ashtray and which is constructed and arranged to direct an incoming flow of air over said smoking article, wherein the incoming flow of air flows across the directional fin before flowing over said smoking article.

2. An ashtray according to claim 1, wherein the directional fin is arranged to guide the flow of air along the axis of the smoking article.

3. An ashtray according to claim 1, wherein the directional fin is at least partially located beneath the ashtray.

4. The ashtray of claim 3, wherein said directional fin protrudes from beneath said ashtray.

5. An ashtray according to claim 1, wherein the directional fin is in the form of a lobe which extends beneath the ashtray.

6. An ashtray according to claim 1, wherein the ashtray has a main body which defines a container for collecting ash.

7. An ashtray according to claim 1, wherein the ashtray comprises a lower member which extends beneath and rearwards of the ashtray main body, and the directional fin is at least partially located on the lower member.

8. An ashtray according to claim 1, wherein the directional fin has a width that decreases with distance from the ashtray.

9. An ashtray according to claim 1, wherein the directional fin forms a smooth surface with the ashtray.

10. An ashtray according to claim 1, wherein the directional fin is arranged to reduce turbulence in the airflow.

11. An ashtray according to claim 1, wherein the directional fin comprises at least one of: a fin body; a tapered guide into the fin; and a tapered guide out of the fin.

12. An ashtray according to claim 1, further comprising an air scoop for deflecting airflow around the bottom of the ashtray.

13. An ashtray according to claim 12, wherein the ashtray comprises a lower member having a surface which is a continuation of the surface of the air scoop.

14. An ashtray according to claim 1, wherein the ashtray is designed and arranged to function with a plurality of smoking articles.

15. An ashtray according to claim 14, wherein the ashtray comprises a plurality of directional fins for directing airflow over the smoking articles.

16. An ashtray according to claim 15, wherein the directional fins are regularly spaced along the leading edge of the ashtray.

17. A smoking machine for smoking a plurality of smoking articles, said smoking machine comprising a plurality of holders for holding the smoking articles, and a plurality of directional fins constructed and arranged for directing an incoming airflow over the smoking articles, wherein the incoming airflow flows across said plurality of directional fins before flowing over said smoking articles.

18. A smoking machine according to claim 17, wherein a directional fin is located between each smoking position.

19. A smoking machine according to claim 17, wherein a directional fin is located between a final smoking position and an outer wall of the smoking machine.

20. A smoking machine according to claim 17, further comprising an ashtray situated under the smoking articles.

21. A smoking machine according to claim 20, wherein the directional fins form part of the ashtray.

22. A smoking machine according to claim 20, wherein airflow is directed from under the ashtray, around a lip of the ashtray and to the smoking article.

23. A smoking machine according to claim 17, wherein the machine comprises an ashtray and an air scoop for deflecting airflow around the bottom of the ashtray.

24. A smoking machine according to claim 17, wherein the air extraction system comprises an open ducting arrangement with a single extraction source.

25. A smoking machine according to claim 17, further comprising balancing baffles arranged to balance the flow of air over the smoking articles.

26. A smoking machine according to claim 17, further comprising puffing means for drawing air through the smoking articles.

27. A method of managing airflow through a smoking machine which is constructed and arranged for smoking a smoking article, the method comprising the following step:
   directing an incoming airflow across a directional fin of said smoking machine before flowing over the smoking article and along the axis of the smoking article.

28. A method according to claim 27, wherein the directional fin forms part of an ashtray.

29. A method according to claim 27, further comprising directing air flow under an ashtray using an air scoop.

* * * * *